United States Patent [19]

Morita et al.

[11] Patent Number: 4,686,471

[45] Date of Patent: Aug. 11, 1987

[54] SYSTEM FOR ONLINE-DETECTION OF THE TRANSFORMATION VALUE AND/OR FLATNESS OF STEEL OR A MAGNETIC MATERIAL BY DETECTING CHANGES IN INDUCED VOLTAGES DUE TO INTERLINKED MAGNETIC FLUXES IN DETECTING COILS

[75] Inventors: Masahiko Morita; Osamu Hashimoto, both of Kurashiki; Tomoo Tanaka, Chiba, all of Japan

[73] Assignee: Kawasaki Steel Corporation, Hyogo, Japan

[21] Appl. No.: 658,606

[22] Filed: Oct. 9, 1984

[51] Int. Cl.[4] ................. G01N 27/72; G01R 33/12
[52] U.S. Cl. ................................ 324/243; 324/225; 324/227
[58] Field of Search ............. 324/220, 221, 227–230, 324/233, 234, 239–243, 225, 207

[56] References Cited

U.S. PATENT DOCUMENTS

| | | | |
|---|---|---|---|
| 2,563,254 | 8/1951 | Lewis | 324/229 |
| 2,810,880 | 10/1957 | Buccicone | 324/243 |
| 3,060,377 | 10/1962 | Schmidt | 324/220 |
| 3,086,168 | 4/1963 | Buckner | 324/221 |
| 3,197,693 | 7/1965 | Libby | 324/233 X |
| 3,434,046 | 3/1969 | Wilson et al. | 324/221 |

FOREIGN PATENT DOCUMENTS

| | | |
|---|---|---|
| 2600453 | 7/1976 | Fed. Rep. of Germany . |
| 2641046 | 3/1977 | Fed. Rep. of Germany . |
| WO83/02159 | 6/1983 | PCT Int'l Appl. . |
| 437342 | 1/1976 | U.S.S.R. .............. 324/229 |
| 970206 | 11/1982 | U.S.S.R. .............. 324/230 |

*Primary Examiner*—Gerard R. Strecker
*Attorney, Agent, or Firm*—Parkhurst & Oliff

[57] ABSTRACT

A system for online-detection of a transformation value and/or a flatness of a steel or a magnetic material includes: an exciting coil disposed at either side of the plate-shaped steel or magnetic material and capable of generating alternating magnetic fluxes by alternating current excitations; two or more detecting coils arranged on the same side as the exciting coil and at positions different in distance from the exciting coil, and mutually induced with the exciting coil; and an arithmetic unit for obtaining the transformation value and the flatness of the steel or the magnetic material or either one of those from a difference between detection signals generated from a difference in values of interlock magnetic fluxes in the respective detecting coils. The transformation value and the flatness of the steel or the flatness of the magnetic material can be detected with high accuracy.

9 Claims, 9 Drawing Figures

SYSTEM FOR ONLINE-DETECTION OF THE TRANSFORMATION VALUE AND/OR FLATNESS OF STEEL OR A MAGNETIC MATERIAL BY DETECTING CHANGES IN INDUCED VOLTAGES DUE TO INTERLINKED MAGNETIC FLUXES IN DETECTING COILS

BACKGROUND OF THE INVENTION

1. Field of the Invention

This invention relates to a system for online-detecting a transformation value and/or the flatness of a steel or a magnetic material.

2. Description of the Prior Art

There are various methods for strengthening steel including work hardening, precipitation hardening, solution hardening, refining of grain size, transformation structure strengthening and the like.

Backed by the recent tendency to reduce manufacturing costs of steel products, there has been activated the utilization of the transformation structure strengthening technique through the controlled cooling after the hot rolling as a measure of manufacturing a higher strength steel in a hot rolled state, using a steel blank having low alloy contents.

Now when the transformation structure strengthening technique is utilized, needless to say, it is necessary to have accurate knowledge about the transformation behavior of steel. The transformation behavior of steel, has been generally studied in an experimental manner in a laboratory. However, in many cases, the transformation behavior of steels which are manufactured by an actual system are different from the results of experiments in the laboratory to a considerable extent. Although the actual conditions have not been fully grasped yet, one of the reasons for the difference of the transformation behavior in the actual system from the results of experiments in the laboratory is said to be that the transformation behavior is complicatedly varied depending upon the history of thermal strains and the like in the preceding process or an upstream process. In consequence, if online information about the transformation behavior of steel could be precisely detected, then a great profit would be expected in the field of manufacturing various steels by means of hot rolling and heat treatment. The profit would be expected because the online information can be used, for example: (A) as a measure of grasping the variations in a local transformation behavior due to a difference in the histories of rolling temperture to improve the homogeneity in the material in the longitudinal and widthwise directions, which is a major factor governing the material quality of a hot-rolled steel; (B) as a measure of grasping a ratio between gamma phase and alpha phase at the time of applying the reduction to manufacture a steel having a high strength and being excellent in toughness, e.g. a steel plate for a high tension line pipe; or (C) as a measure of grasping a ratio of gamma phase and alpha phase at the time of starting the quenching in the manufacturing technique of a mixed structure steel to manufacture a thin steel plate having a high strength and being excellent in workability.

Heretofore, there has been proposed the following method as a method of online-detecting the above-described transformation behavior of steel. In one method, the rise in temperature due to the latent heat at the time of the phase transformation is detected by a thermometer installed on a manufacturing line to grasp a transformation behavior as described in Japanese patent publication No. 24017/81 for example. However, this method is disadvantageous in that obtainable information is given in excessively broad outline, the response is slow and the thermometer is used as a sensor, with the result that the measurement during water cooling cannot be conducted.

Furthermore, as described in Japanese patent laid-open Nos. 114518/74, 136442/76 and Japanese patent publication No. 25309/78, there have been proposed methods, in which X-rays are irradiated onto the surface of a steel, and the transformation value is measured from a diffraction strength. However, this method is disadvantageous in that it is necessary to take safety protective measure from the X-ray injuries since strong X-rays are irradiated, and consequently, the detection system itself becomes large-sized, resulting in increased installation cost, a limited installed number, occurrence of maintenance problems and the like. Additionally, since the obtainable information remains only within the surface layer portion of about 50 micro meters or less of the material to be measured, the information thus obtained cannot be used as macroscopic information.

In contrast thereto, there have been proposed methods of detecting the transformation behavior by use of a magnetic detector, utilizing the fact that the transformation from gamma phase to alpha phase of steel is accompanied by a physical phenomenon of a change from the paramagnetism (gamma phase) to the ferromagnetism (alpha phase). For example, Japanese patent laid-open Nos. 104754/75 and 82443/81 correspond to these proposals. These methods are problematical in that the measurable temperature range is limited to a temperature region of the Curie point or less of the steel to be measured. However, in most cases, the Curie points of ordinary commercial steels are as high as about 750° C. In contrast thereto, the range of transformation of the steel during cooling process is transfered in non-equilibrium condition to the low temperature side, whereby the most part of transformation proceeds within a temparature range of the Curie point or less. These methods are advantageous in that the above-mentioned problems do not impose practical obstacles except for some types of steels, and are used easier in practice and the response is good as compared with other methods not utilizing the aforesaid magnetic means. Moreover, the measurements are practicable during water cooling and so on, thereby proving to practical and effective methods. However, it cannot be said that these detecting systems are satisfactory, because the magnetic detecting systems proposed by Japanese patent laid-open Nos. 104754/75 and 82448/81 have the following problems which are not solved yet:

Firstly, description will be given of Japanese patent laid-open No. 104754/75. This proposal relates to a hot rolling method utilizing a magnetic detecting system, not relating to the magnetic detecting system itself, thus the details about the fuctions and construction of the detecting system in the practical use are unclear. However, according to the description in the specification of the proposal, an excited pickup coil is placed close to the steel to be measured, and the presence of transformation is qualitatively detected from a change in impedance of the pickup coil itself generated due to the transformation of the steel to be measured from gamma phase to alpha phase. However, in order to apply the proposal to the manufacturing field of steel as aforesaid, it is necessary to have a function capable of quantitatively detecting the progress of transformation as the function of the magnetic detecting device. With the detecting device capable of only qualitatively detecting the presence of the transformation as described in the proposal, it should be said that the value of application is low.

Figure 1:
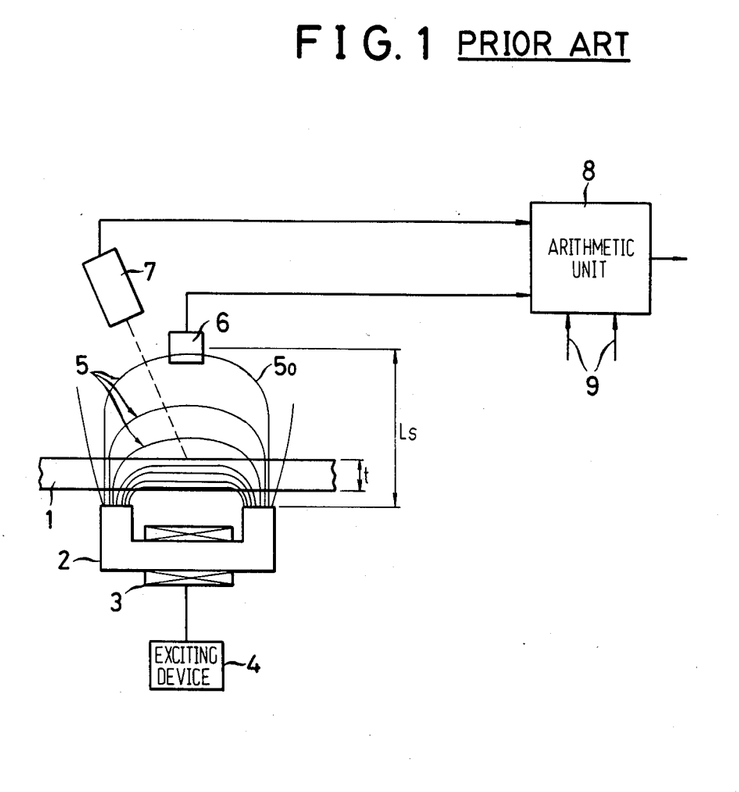
FIG. 1 is a partially sectional block diagram showing the conventional example of the magnetically measuring type transformation value detecting system.

Description will now be given of Japanese patent laid-open No. 82443/81. FIG. 1 is a block diagram showing the arrangement of the magnetic detecting system in this proposal. This magnetic detecting system is of such an arrangement that an exciting coil 3 wound around a magnetic pole 2 composed by a U-shaped iron core and magnetic flux detector 6 are spaced a predetermined distance Ls from each other. A steel 1 as being a material to be measured is interposed therebetween, and the exciting coil 3 is excited by an exciting device 4, whereby, out of magnetic fluxes 5 generated by the excitation, the intensity of a magnetic flux 5o which penetrates through the steel 1 and is leaked to reach the flux detector 6 is detected. The transformation value is detected from a change in intensity of the flux 5o generated in accordance with a transformation value in the steel 1. In the drawing, designated at 7 is a thermometer, 8 an arithmetic unit, and 9 condition signals of the material, of plate thickness and the like. Although this method has a function capable of quantitatively measuring the transformation value in principles as compared with the aforesaid Japanese patent laid-open No. 104754/75, it has the following disadvantages in the application to an actual manufacturing line.

Namely, in the above arrangement, the intensity of the magnetic flux 5o (magnetic flux density) is substantially inversely proportional to the distance Ls between the magnetic pole 2 and the magnetic flux detector 6, and hence, in order to detect the transformation value with satisfactory accuracy, it is necessary to make the distance Ls to be at least about 150 mm or less. However, it should be said that it is extremely difficult to move the steel 1 through such a narrow gap without contacting the magnetic flux detector 6 in the application of the proposal to the actual manufacturing line. This is because a hot-rolled steel plate manufactured in a hot strip mill and plate mill for example should not necessarily be flat due to buckling, camber, waving, and/or the like. This tendency is particularly strong in the forward end, rear end and therearound of the rolled steel and hence, contact of the detector 6 with the steel 1 is inevitable during conveyance of the steel. In order to avoid such an accident, there is proposed such a method that the aforesaid gap is temporarily expanded during the passing therethrough by the forward end or rear end portion of the steel for example. However, the variability in material quality tends to occur in the forward end, rear end portion or therearound, and hence, if it is impossible to detect these portions, then the value of installing the detecting device should be lost by half. Furthermore, the magnetic detecting system of the proposal is disadvantageous in that, since a vacant space portion in a magnetic circuit through which the magnetic fluxes 5 are passed is varied depending upon the difference in plate thickness t of the steel 1 as being the material to be measured, it is necessary to correct a detection output by the plate thickness t. Further, the measuring accuracy depends upon the actual plate thickness t, and so on. However, the plate thickness t of the steel 1, which is rolled by an ordinary hot rolling mill is widely varied in such ways as 1.2–30 mm in a hot strip mill and 5.0–300 mm in a plate mill for example. The correcting operations are complicated, and it is difficult from the viewpoint of the characteristics of the conveyance of the steel 1 to substantially obtain the proper detecting accuracy in accordance with the actual plate thickness t.

As described above, it should be said that the magnetic detecting system proposed by Japanese patent laid-open No. 82443/81 has many problems in the application to the actual manufacturing line.

SUMMARY OF THE INVENTION

The present invention has been developed to obviate the above-described disadvantages of the prior art and has as its first object the provision of a magnetic detecting system which is multiply functional, wherein a transformation value of a steel, which has not been detectable by the conventional method, is precisely detected, and further, even the flatness of the steel can be detected with high accuracy at the same time.

A second object of the present invention is to provide a magnetic detecting system capable of detecting the flatness of a magnetic material with high accuracy.

To accomplish the first object, the present invention contemplates that, in a system for online-detecting a transformation value and/or a flatness of a steel, the system comprises:

an exciting coil disposed at either one side of the plate-shaped steel as being the material to be measured and capable of generating alternating magnetic fluxes by alternating current excitations;

two or more detecting coils arranged on the same side as the exciting coil and at positions different in distance from the exciting coil, and mutually induced with the exciting coil; and an arithmetic unit for obtaining the transformation value and the flatness of the steel or either one of those from a difference between detection signals generated from a difference in values of interlink magnetic fluxes in the respective detecting coils.

A specific form of the present invention is of such an arrangement that the two or more detecting coils are disposed within a range of 200 mm or less from the exciting coil, respectively, and spaced 20 mm or more apart from each other, so that high detecting accuracy can be reliably obtained.

Another specific form of the present invention is of such an arrangement that one of the detecting coils is disposed concentrically with the exciting coil, so that a space for installation can be minimized.

A further specific form of the present invention is of such an arrangement that at least one coil out of the exciting coil and the detecting coils is provided therein with a core for exclusive use, which does not stride over any one of other coils, so that magnitudes of detection signals can be greatly increased.

A still further specific form of the present invention is of such an arrangement that only the exciting coil is provided therein with a rod-shaped core, so that the exciting magnetic field is increased in its intensity.

A still further specific form of the present invention is of such an arrangement that independent rod-shaped cores are provided in all of the exciting coil and the detecting coils, respectively, so that the magnitudes of the detection signals can be maximised.

A still further specific form of the present invention is of such an arrangement that all of the exciting coil and the detecting coils are commonly provided with a comb-shaped core striding over all of the coils, so that the installation work can be facilitated.

A still further specific form of the present invention is of such an arrangement that a frequency of exciting current applied to the exciting coil is held within a range of 5 Hz–10 KHz so that the suitable penetrating depth of magnetic fluxes, the good response speed of the detecting device, the high S/N ratio (Signal to Noise ratio) between the detection signals and the like can be obtained respectively.

To accomplish the second object, the present invention contemplates that, in a system for online-detecting a flatness of a magnetic material, the system comprises:

an exciting coil disposed at either one side of the plate-shaped magnetic material as being the material to be measured and capable of generating alternating magnetic fluxes by alternating current excitations:

two or more detecting coils arranged on the same side as the exciting coil and at positions different in distance from the exciting coil, and mutually induced by the exciting coil; and an arithmetic unit for obtaining the flatness of the magnetic material from a difference between detection signals generated from a difference in values of interlink magnetic fluxes in the respective detecting coils.

As described above, according to the present invention, two or more detecting coils are arranged on the same side as the exciting coil and at positions different in distance from the exciting coil and the transformation value and the flatness (lift-off) of a steel as being the material to be measured are simultaneously sought by the detecting signals, so that the following advantages are obtainable.

(A) The mutual induction by the magnetism is utilized for the detection, so that the detection is accurate, the response is good and the system is excellent as an online quantitative detecting means.

(B) The components of the detecting system can be concentrically disposed on one side of the material to be measured, so that, even in the manufacturing line where the flatness of the material is not so good, the system is satisfactorily practicable.

(C) Although the components are disposed at one side of the material, the transformation value of the steel can be detected with the system not being subjected to the influence of the fluctuations in lift-off.

(D) The online information on the lift-off, i.e. the flatness of the material can be collectively or singly detected.

(E) While the flatness of the material can be detected by the magnetic detection, the system is not subjected to the influence of the transformation value of the steel.

(F) The system is widely usable in the various cases including ambient conditions of high temperature, under water and the like.

In consequence, not only the online detection of the transformation value of the steel in the various hot rolling processes and heat treatment processes, but also the online detection of the flatness are simultaneously conducted. Further, the detection should not necessarily be limited to steel, since if the material to be measured may give some influence to the mutual induction between the exciting coil and the detecting coils, the flatness of the material to be measured can be online-detected irrespective of the presence of the transformation behavior. Thus, the system can be applied to uses of a very wide range.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Detailed description will hereunder be given of the present invention with reference to the accompanying drawings.

Figure 2:
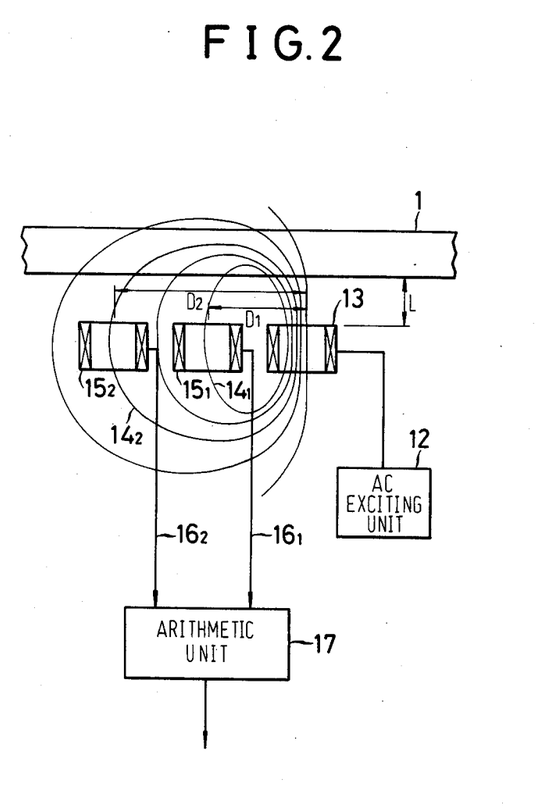
FIG. 2 is a block diagram corresponding to FIG. 1, showing a first embodiment of the present invention.

FIG. 2 shows the first embodiment of the present invention. In the drawing, designated at 1 is a steel being the material to be measured, 12 an alternating current (AC) exciting device, 13 an exciting coil, and $15_1$ and $15_2$ detecting coils disposed at positions different in distance ($D_1$ and $D_2$) from the exciting coil 13. Denoted at $14_1$ is a magnetic flux generated at the exciting coil 13 and interlinked with the detecting coil $15_1$ through the steel 1 and $14_2$ a magnetic flux interlinked with the detecting coil $15_2$.

When the steel 1 does not begin to transform, the steel 1 is in the single gamma phase, i.e., the paramagnetic condition. In this state (hereinafter referred to as "the initial state"), the magnetic fluxes $14_1$ and $14_2$ interlinked with the detecting coils $15_1$ and $15_2$ have predetermined intensities corresponding to the distances $D_1$ and $D_2$ from the exciting coil 13 and induced voltages proportional to the predetermined intensities, respectively.

When the steel 1 begins to transform from gamma phase to alpha phase and a paramagnetic alpha phase precipitates, the alpha phase is magnetized, fluctuations are caused to the intensity of magnetic field of the steel 1, and the intensities of the magnetic fluxes $14_1$ and $14_2$ are shifted from the initial state, whereby the results are detected as the changes in the induced voltages in the detecting coils $15_1$ and $15_2$. Furthermore, when a distance L between the steel 1 and the exciting coil 13 (hereinafter referred to as a "lift-off", and the term measuring the lift-off" indicates measuring the flatness) is varied, the induced voltages at the detecting coils $15_1$ and $15_2$ are changed, respectively. Detection signals $16_1$ and $16_2$ thus obtained at the detecting coils $15_1$ and $15_2$ are delivered to an arithmetic unit 17, where the magnitudes of the signals measured at the detecting coils $15_1$ and $15_2$ are compared, and a transformation value and a lift-off L are separately calculated in accordance with the relationship to be described hereunder, which is previously stored in the arithmetic unit 17.

Description will now be given of a technique of obtaining the transformation value in the steel 1 and the lift-off L from the magnitudes of the detection signals $16_1$ and $16_2$ of the detecting coils $15_1$ and $15_2$.

Figure 3:
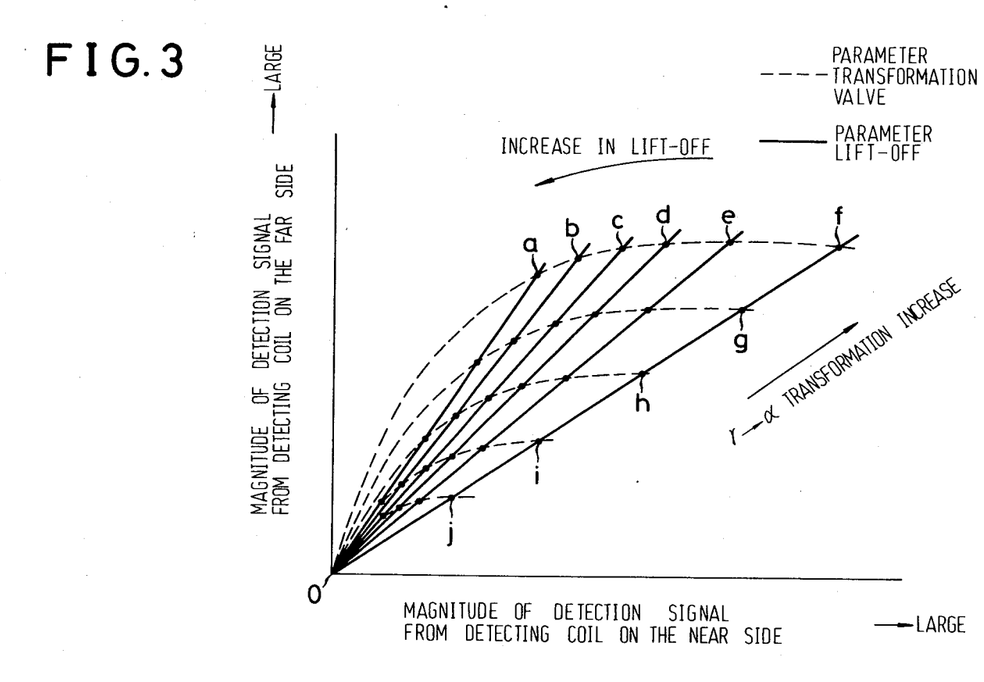
FIG. 3 is a chart showing the interrelation of the increase or decrease of the lift-off and transformation value with the detection signals at the detecting coils, in explanation of the principles of the present invention.

FIG. 3 shows the relationship between the detection signals (varied values in the induced voltages from the initial state ) of the detecting coils $15_1$ and $15_2$ when the gamma to alpha transformation value of the steel 1 and the lift-off L are varied in a detecting system basically following the arrangement shown in FIG. 2, wherein the distance $D_1$ from the exciting coil 13 to the detecting coil $15_1$ is made to be 50 mm and the distance $D_2$ from the exciting coil 13 to the detecting coil $15_2$ is made to be 100 mm. In FIG. 3, those curves indicated by broken lines are relationships in the cases where the transformation values are at constant values and only the lift-off L is varied, and those curves indicated by solid lines are relationships in the cases where the lift-off L are at constant values and only the transformation value is varied. As apparent from FIG. 3, the relationship in magnitude between the detection signals $16_1$ and $16_2$ of the detecting coils $15_1$ and $15_2$ assumes a curved line as shown in 0 - a - b - c - d - e - f when the lift-off L is varied, whereas the aforesaid relationship assumes a generally straight line as shown in 0 - j - i - h - g - f when the transformation value is varied. Namely, it is found that vector quantities determined by the detection signals $16_1$ and $16_2$ of the two detecting coils $15_1$ and $15_2$ have intrinsic relationships with the transformation value and the lift-off L, respectively. In consequence, the precise relationships shown in FIG. 3 are previously obtained, stored in the arithmetic unit 17 shown in FIG. 2, and compared with the detection signals $16_1$ and $16_2$ detected by the detecting coils $15_1$ and $15_2$ for calculation, so that the transformation value and the lift-off L can be simultaneously obtained.

In the foregoing, description has been given of the case where two detecting coils are used. It is natural that the same thing should be true of the cases where the number of the detecting coils is more than two. Needless to say, when the number of the detecting coils is increased, whereby measurements by use of three or four detecting coils are conducted, a further precise measurement can be accomplished. As apparent from the above description, according to the present invention with the above-described arrangement, information on "only the transformation value", "the transformation value and the flatness" or "only the flatness" can be selectively obtained as necessary. When obtaining the information on "only the flatness", the material to be measured need not necessarily be limited to the "steel", and any material to be measured will do, only if the material to be measured gives some influence on the mutual induction effect between the exciting coil and the detecting coils. In consequence, when only the information on the flatness as described above is required, the term "steel" is reread as "a steel or any other material having in its composition a material providing an influence on the mutual induction effect between the exciting coil and the detecting coils" i.e. "magnetic material", including the term used in the claims. Needless to say, when either one of the information is required, it suffices only if the information on the aforesaid either one of the information is outputted.

Description will hereunder be given of the preferable specific form in the stage of specifically working the present invention.

Figure 4:
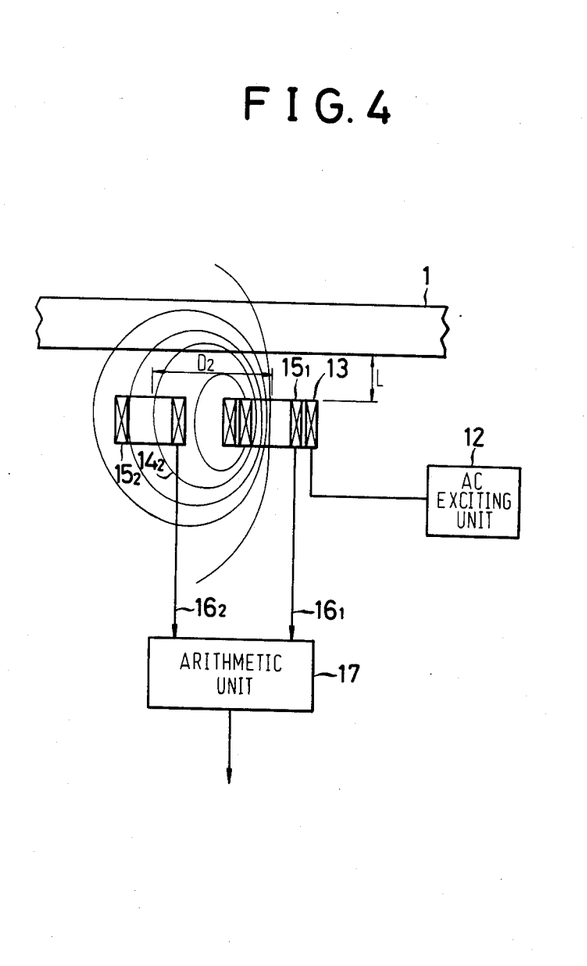
FIG. 4 is a block diagram corresponding to FIG. 2, showing a second embodiment of the present invention.
Figure 5:
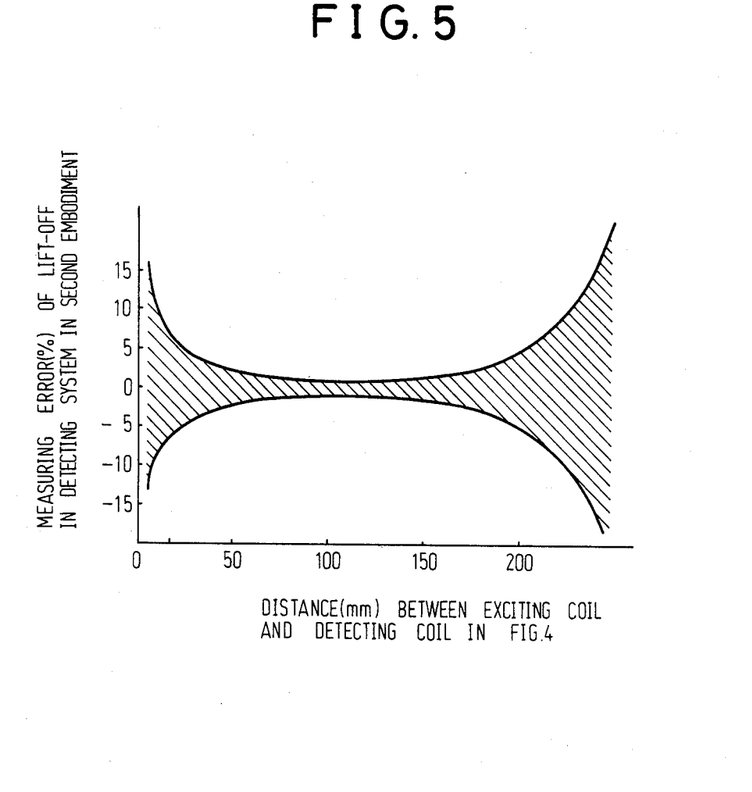
FIG. 5 is a chart showing the relationship of the intervals between the detecting coils with the measuring errors in lift-off.

Firstly, the arrangement of the detecting coils and the exciting coil will be described. FIG. 4 shows the second embodiment of the present invention, which is identical in basic arrangement with the first embodiment shown in FIG. 2, however, the detecting coil $15_1$ is disposed concentrically with the exciting coil 13. FIG. 5 shows the detecting accuracy of the lift-off L when the distance $D_2$ between the exciting coil 13 and the detecting coil $15_2$ is varied in some way or other in the detecting system shown in FIG. 4. As apparent from this, when $D_2$ is less than 20 mm or beyond 200 mm, the detecting accuracy of the lift-off L tends to be deteriorated, and consequently, it is found that there is an optimum range for $D_2$ to obtain the satisfactory detecting accuracy. The above-described tendency is true of the detecting accuracy of the transformation value. It is appreciated that this is because of the following reasons. Namely, when $D_2$ is beyond 200 mm, the detecting signal $16_2$ of the detecting coil $15_2$ as shown in FIG. 4 becomes considerably small in magnitude, whereby the detecting signal is easily subjected to an influence of noises and the like, so that the S/N ratio is deteriorated. Whereas, when $D_2$ is less than 20 mm, the difference in the ways of sensitivity to the transformation value and the lift-off L at the detecting coils $15_1$ and $15_2$ as shown in FIG. 4 becomes very low, whereby it becomes difficult to separate the transformation value and the lift-off L from the detection signals $16_1$ and $16_2$ for quantitative measuring, so that the detecting accuracy is deteriorated. As apparent from the above knowledge, according to the present invention, it is preferable that the detecting coils are disposed within a radial range of 200 mm from the center of the exciting coil in a manner to be spaced 20 mm or more apart from each other.

Description will now be given of the effect of the cores. As one of its drawbacks, the magnetic detecting system has the general characteristics that the magnitudes of the detection signals become smaller in an inverse proportion to the increase of the lift-off, whereby the range of detectable lift-off is restricted. It goes without saying that, when the magnetic detecting system is applied to the actual manufacturing line, it is preferable that the above-described range is as large as possible from the viewpoint of not only the detecting accuracy but also the heat resistance of the detecting system, the conveyance characteristics, the shape and the like of the material to be measured. The present invention has been developed in view of the above respects, with the result that it has been found that the independent cores for exclusive use are provided in the exciting coil and the detecting coils as necessary, so that the magnitudes of the detection signals in the same lift-off can be increased to a considerable extent.

Figure 6:
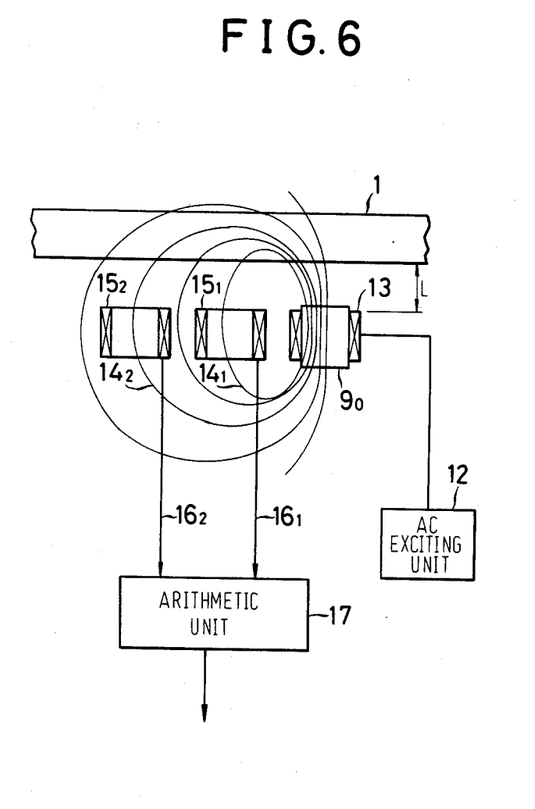
FIGS. 6 to 8 are block diagrams corresponding to FIG. 2, showing third to fifth embodiments of the present invention.
Figure 7:
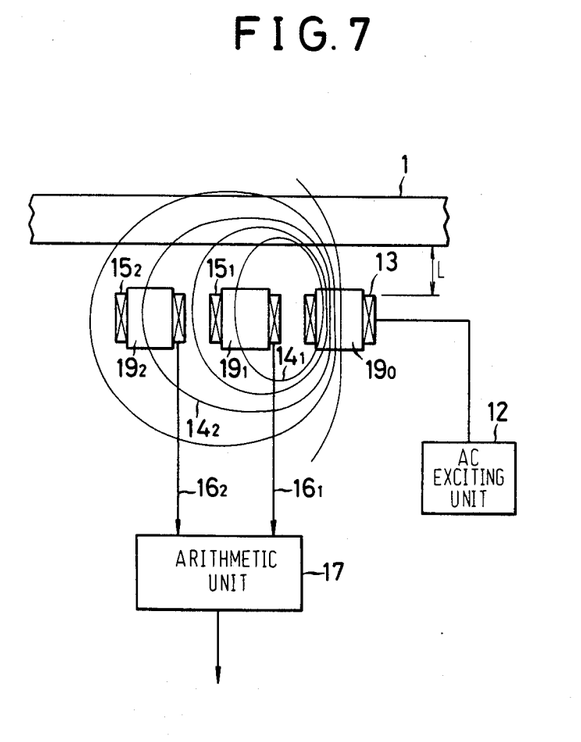
Figure 8:
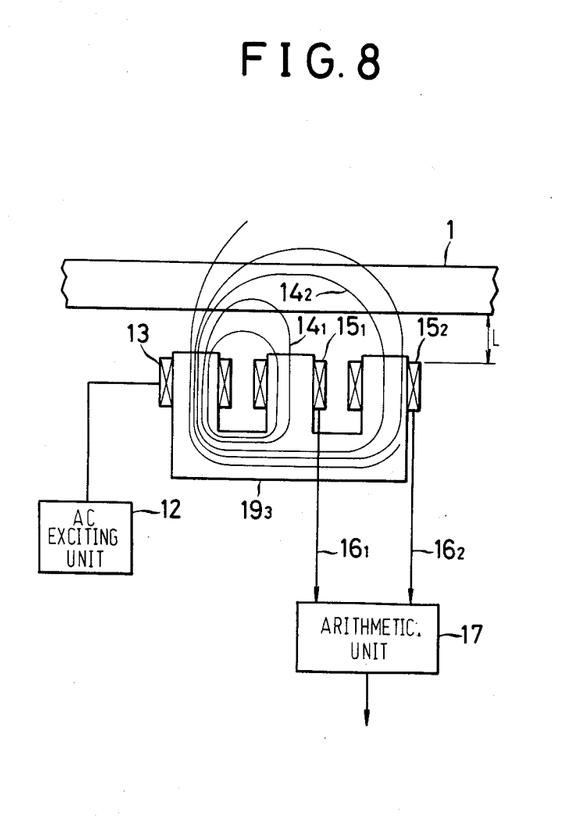
Figure 9:
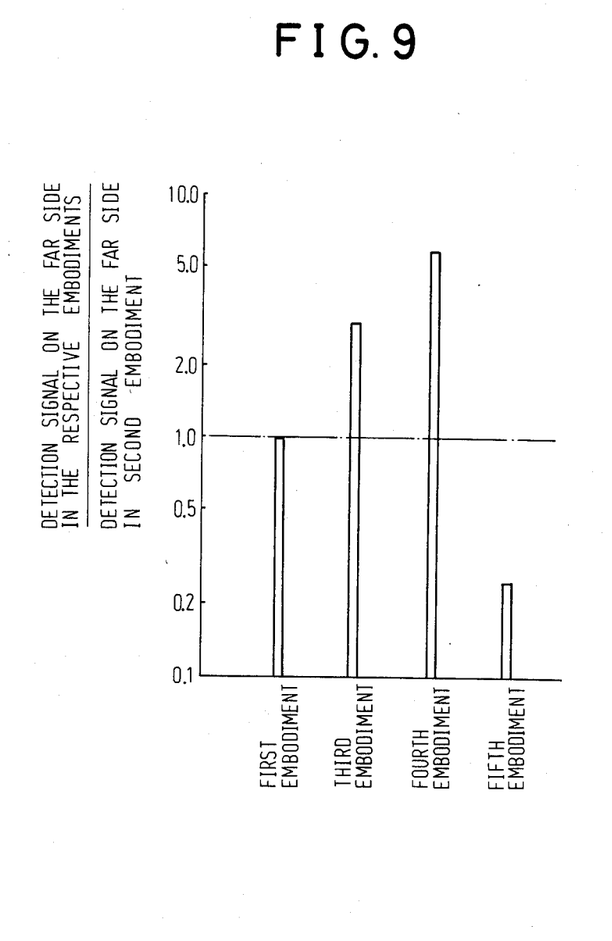
FIG. 9 is a chart showing the relationship of the respective embodiments with the second embodiment about the magnitudes of the detection signals when the core is provided in the exciting coil or the detecting coils.

FIGS. 6 to 8 show the third to fifth embodiments of the present invention, where the cores are provided in some coils, respectively. FIG. 6 shows the case where a rod-shaped core $9_0$ is provided in the exciting coil 13, and FIG. 7 shows the case where rod-shaped cores $19_0$, $19_1$ and $19_2$ are provided in the exciting coil 13, the detecting coils $15_1$ and $15_2$, respectively. FIG. 8 shows the case where the exciting coil 13, the detecting coils $15_1$ and $15_2$ are connected to one another by an E-shaped core $19_3$. FIG. 9 shows that the magnitudes of the detection signals $16_2$ detected by the respective detecting systems shown in FIG. 2 and FIGS. 6 to 8 are compared with the magnitude of the detection signal $16_2$ as being the reference at the detecting coil $15_2$ under the same conditions where the transformation rate gamma phase—alpha phase of the steel 1 is 100% and the lift-off L is 100 mm, by use of the detecting system of the second embodiment shown in FIG. 4. Additionally, the results shown in FIG. 9 are obtained under the same conditions except those relating to the core or cores.

FIG. 9 makes it clear that the magnitude of the detection signal $16_2$ tends to increase in the case where the rod-shaped core $19_0$ is provided in the exciting coil 13 in FIG. 6 (the third embodiment) and also in the case where the rod-shaped cores $19_0$, $19_1$ and $19_2$ are provided in the exciting coil 13, the detecting coil $15_1$ and $15_2$, respectively, in FIG. 7 (the fourth embodiment) as compared with the case where no core is provided as in FIG. 4 (the second embodiment). In consequence, it is found that the provision of the rod-shaped cores $19_0$–$19_2$ makes it possible to improve the detecting accuracy in the region where the lift-off L is large. Additionally, in the case of the fifth embodiment where the E-shaped core $19_3$ shown in FIG. 8 is provided, within the range of the lift-off L of 50 mm or less, the magnitude of the detection signal $16_2$ is large as compared with other embodiments of the present invention. However, as the lift-off L increases beyond 50 mm, the magnitude of the detection signal $16_2$ sharply decreases in magnitude. As apparent from FIG. 9, it is recognized that the magnitude of the detection signal $16_2$ rather decreases in the conditions where the lift-off is 100 mm. In consequence, this fifth embodiment proves to work satisfactorily when applied to a relatively small-sized line where the steel 1 as being the material to be measured has a satisfactorily good flatness.

Description will hereunder be given of the preferable exciting conditions in the present invention. As well known tody, penetrating depth of the magnetic flux into the magnetic material largely depends upon the frequency of the magnetic flux. In other words as the exciting frequency of the exciting coil in the detecting system becomes higher, the penetrating depth into the material to be measured decreases. Now, it is known that, in general, the steel after the hot rolling shows a peculiar transformation behavior under the surface layer due to the influence of the temperature distribution, the rolling or the like, the detection information as described above in such a peculiar region as described above tends to reduce the significance in relating the steel to the material quality in the final product. In consequence, during measurements, it is desired to make the exciting conditions of the detecting system proper. According to the research of by the inventors of the present invention, the region, in which the transformation characteristics of the hot-rolled steel shows the peculiar behavior, is within a range of about 200 micro meters under the surface layer. In order to avoid it, it is desirable to make the penetrating depth of the magnetic flux to be 200 micro meters or more. So, it is desirable to make the frequency of the exciting current in the detecting system to be 10 KHz or less in view of the above. Namely, the lower the frequency becomes, the larger the penetrating depth of the magnetic flux becomes, and accordingly, the information on the transformation value detected becomes more macroscopic. On the other hand, there are presented such drawbacks as the deterioration in the speed of response of the detecting system and the lowering of the S/N ratio of the detection signals. In order to avoid the above-described drawbacks, it is desirable that the exciting frequency is not less than 5 Hz. The most preferable range of the exciting frequency is 30 Hz–1 KHz.

It should be apparent to those skilled in the art that the above-described embodiments are merely representative, which represent the applications of the principles of the present invention. Numerous and varied other arrangements can be readily devised by those skilled in the art without departing from the spirit and the scope of the invention.

What is claimed is:

1. A system for online-detection of a transformation value and/or a flatness of a steel comprising:
   an exciting coil located at a spaced distance from one side of the surface of the steel and capable of generating alternating magnetic fluxes by alternating current excitations;
   at least two detecting coils arranged on the same side and at substantially the same spaced distance from said steel as said exciting coil, said detecting coils being arranged at positions different in distance from said exciting coil in a direction parallel to the surface of said steel, and having induced voltages due to the magnetic fluxes generated by said exciting coil; and
   an arithmetic unit for calculating and outputting the transformation value and the flatness of said steel or either one of those, said arithmetic unit being independently electrically coupled with each of said detecting coils such that values of the induced voltages in the detecting coils are input into said arithmetic unit and at least one of the transformation value and the flatness of said steel is calculated by the arithmetic unit in accordance with a predetermined formula using the values of the induced voltages.

2. A system for online-detection of a transformation value and/or the flatness of a steel as set forth in claim 1, wherein said two or more detecting coils are disposed within a range of 200 mm or less from said exciting coil, respectively, and spaced 20 mm or more apart from each other.

3. A system for online-detection of a transformation value and/or the flatness of a steel as set forth in claim 1, wherein one of said detecting coils is disposed concentrically with said exciting coil.

4. A system for online-detection of the transformation value and/or the flatness of a steel as set forth in claim 1, wherein at least one of said exciting coil and said detecting coils is provided therein with a core which is not connected with any one of other coils.

5. A system for online-detection of a transformation value and/or the flatness of a steel as set forth in claim 4, wherein a rod-shaped core is provided only in said exciting coil.

6. A system for online-detection of a transformation value and/or the flatness of a steel as set forth in claim 4, wherein independent rod-shaped cores are provided in all of said exciting coil and said detecting coils, respectively.

7. A system for online-detection of a transformation value and/or the flatness of a steel as set forth in claim 1, wherein said exciting coil and said detecting coils are commonly provided with a comb-shaped core connected to all of said coils.

8. A system for online-detection of a transformation value and/or the flatness of a steel as set forth in claim 1, wherein a frequency of exciting current applied to said exciting coil is held within a range of 5 Hz–10 KHz.

9. A system for online-detection of a flatness of a magnetic material comprising:

an exciting coil located at a spaced distance from one side of the surface of the magnetic material and capable of generating alternating magnetic fluxes by alternating current excitations;

at least two detecting coils arranged on the same side and at substantially the same spaced distance from said magnetic material as said exciting coil, said detecting coils being arranged at positions different in distance from exciting coil in a direction parallel to the surface of said magnetic material, and having induced voltages due to the magnetic fluxes generated by said exciting coil; and an arithmetic unit for calculating and outputting the flatness of said magnetic material, said arithmetic unit being independently electrically coupled with each of said detecting coils such that values of the induced voltages in the detecting coils are input into said arithmetic unit and the flatness of said magnetic material is calculated by the arithmetic unit in accordance with a predetermined formula using the values of the induced voltages.

* * * * *